(12) United States Patent
Carlson et al.

(10) Patent No.: US 8,246,595 B2
(45) Date of Patent: Aug. 21, 2012

(54) ABSORBENT ARTICLE WITH LEAK BARRIERS

(75) Inventors: Ulrika Carlson, Billdal (SE); Hans Een, Mölnlycke (SE); Jan Wästlund-Karlsson, Mölndal (SE)

(73) Assignee: SCA Hygiene Products AB, Göteborg (SE)

( * ) Notice: Subject to any disclaimer, the term of this patent is extended or adjusted under 35 U.S.C. 154(b) by 542 days.

(21) Appl. No.: 12/294,444

(22) PCT Filed: Apr. 5, 2006

(86) PCT No.: PCT/SE2006/000412
§ 371 (c)(1),
(2), (4) Date: Sep. 25, 2008

(87) PCT Pub. No.: WO2007/114744
PCT Pub. Date: Oct. 11, 2007

(65) Prior Publication Data
US 2010/0228219 A1 Sep. 9, 2010

(51) Int. Cl.
*A61F 13/15* (2006.01)
*A61F 13/20* (2006.01)
(52) U.S. Cl. ........ 604/385.28; 604/385.24; 604/385.101
(58) Field of Classification Search ............. 604/385.01, 604/385.04, 385.101, 385.27
See application file for complete search history.

(56) References Cited

U.S. PATENT DOCUMENTS

| | | | |
|---|---|---|---|
| 4,936,839 A | 6/1990 | Molee et al. | |
| 5,167,653 A | 12/1992 | Igaue et al. | |
| 5,575,785 A | 11/1996 | Gryskiewicz et al. | |
| 5,667,609 A | 9/1997 | Liu | |
| 6,562,015 B1 * | 5/2003 | Wilson | 604/385.01 |
| 6,620,145 B2 | 9/2003 | Nakaoka et al. | |
| 6,790,203 B2 * | 9/2004 | Een | 604/385.28 |
| 7,094,227 B2 | 8/2006 | Ishiguro et al. | |
| 2003/0114827 A1 | 6/2003 | Peterson | |
| 2003/0139724 A1 | 7/2003 | Ragnarson et al. | |
| 2003/0171732 A1 | 9/2003 | Heyrman et al. | |
| 2004/0127882 A1 | 7/2004 | Weber | |
| 2004/0133181 A1 | 7/2004 | Ishiguro et al. | |

(Continued)

FOREIGN PATENT DOCUMENTS

EP 0 219 326 A2 4/1987

(Continued)

OTHER PUBLICATIONS

An English Translation of the Office Action issued in corresponding Russian Application No. 2008143403 dated Nov. 20, 2009.

(Continued)

*Primary Examiner* — Michele M Kidwell
(74) *Attorney, Agent, or Firm* — Buchanan Ingersoll & Rooney PC

(57) ABSTRACT

An absorbent article having a front region, a back region and a crotch region there between, said article has substantially longitudinally extending leak barriers, each of said leak barriers having a free laterally inward elasticized side and a laterally outward side, the elasticized side of the leak barrier being raised from the inner cover of the absorbent article. The crotch region along a length of at least 2 cm, preferably at least 5 cm and more preferably at least 10 cm, in longitudinal direction is free from raised leak barriers, while raised leak barriers are present in the front and/or back regions of the article.

12 Claims, 4 Drawing Sheets

U.S. PATENT DOCUMENTS

| | | |
|---|---|---|
| 2007/0233034 A1 | 10/2007 | Hildeberg et al. |
| 2007/0293833 A1 | 12/2007 | Wennerback |

FOREIGN PATENT DOCUMENTS

| | | |
|---|---|---|
| EP | 0 304 957 A2 | 3/1989 |
| EP | 0 750 895 A2 | 1/1997 |
| EP | 0 913 137 | 5/1999 |
| EP | 0 969 784 A 2 | 1/2000 |
| EP | 1 035 818 | 4/2002 |
| EP | 1 219 271 A2 | 7/2002 |
| EP | 1 384 459 A1 | 1/2004 |
| FR | 2 810 879 A1 | 1/2002 |
| GB | 2 284 538 A | 6/1995 |
| JP | 02-174845 A | 7/1990 |
| JP | 2002-058703 A | 2/2002 |
| JP | 2006-051269 A | 2/2006 |
| WO | WO 97/29722 A1 | 8/1997 |
| WO | WO 98/43571 A1 | 10/1998 |
| WO | WO 99/27876 A1 | 6/1999 |
| WO | WO 02/49560 A1 | 6/2002 |
| WO | WO 2004/060251 A1 | 7/2004 |
| WO | WO 2005/122985 A1 | 12/2005 |
| WO | WO 2006/093439 A1 | 9/2006 |
| WO | WO 2007/114744 A1 | 10/2007 |

OTHER PUBLICATIONS

International Search Report for PCT/SE2006/000412, completed Oct. 31, 2006.

Written Opinion of the International Searching Authority for PCT/SE2006/000412.

International Preliminary Report on Patentability for PCT/SE2006/000412, completed Mar. 27, 2008.

Extended European Search Report dated May 11, 2011, in corresponding European Patent Application No. 06733273.4.

* cited by examiner

ABSORBENT ARTICLE WITH LEAK BARRIERS

TECHNICAL FIELD

The present disclosure refers to an absorbent article, such as a diaper, pant diaper, incontinent brief, sanitary napkin and the like intended to absorb and retain body fluid of the wearer.

BACKGROUND OF THE DISCLOSURE

Absorbent articles of the above mentioned kind are known, which have longitudinally extending leak barriers alongside the absorbent structure. These leak barriers, also called containment or barrier flaps, have a free laterally inward elasticized side and a laterally outward side, wherein the elasticized side of the leak barrier is raised from the inner cover of the absorbent article. Such raised leak barriers help to reduce the occurrence of leakage of body exudates from the absorbent articles.

U.S. Pat. No. 6,620,145 discloses a diaper provided with raisable leak barriers, which in the crotch area of the diaper are adhered to the body facing sheet of the article at a location inwardly of the laterally outward side of the leak barrier, so that the raised height of the leakage barrier is less in the crotch region than in the front and back regions of the diaper.

US 2004/0127882 discloses a pant diaper provided with leak barriers having a laterally outward side that follows the contours of the leg openings of the diaper.

WO 97/29722 discloses a method of attaching a leak barrier to an absorbent article in a curved manner. The leak barrier has at least one edge parallel to the longitudinal centerline of the article and is bonded to the article along a juncture line that extends in a curved configuration with respect to the longitudinal centerline of the article.

JP 2002-058703 discloses a method of forming a diaper cover from a rectangular piece of material. Leg holes are cut inside the longitudinal side edges of the piece of material, which is then folded inwards along longitudinal folding lines crossing the holes, so as to create an inwardly directed leg contour in each longitudinal side edge. The inwardly folded portions are elasticized to form leak barriers having a lower height in the crotch area.

Absorbent articles having an improved comfort by narrowing the width of the area where the article is applied in the crotch of the wearer (crotch area) during use are known through a number of prior art documents, for example EP-A-1 384 459. A problem may occur when applying leak barriers to absorbent articles having a narrow crotch width, which is that the leak barriers, especially when not completely raised from the body facing coversheet of the article, may partly block the entry of body fluid into the crotch area of the article, which may lead to leakage of body fluid out of the article.

OBJECT AND SUMMARY

One object of embodiments of the present invention is to provide an absorbent article combining properties of comfort and fit in the crotch region and an effective leakage protection. The article comprises substantially longitudinally extending leak barriers of the above mentioned kind, wherein the crotch region of the article along a length of at least 2 cm, preferably at least 5 cm and more preferably at least 10 cm, in longitudinal direction is free from raised leak barriers, while raised leak barriers are present in the front and/or back regions of the article.

According to one embodiment at least part of the crotch region has a width in transverse direction of no more than 20 cm, preferably no more than 15 cm.

In one embodiment, the distance in transverse direction between the laterally outward sides of the leak barriers is at least 3 cm.

In a further embodiment the distance in transverse direction between the laterally outward sides of the leak barriers is at least equal to or larger than, preferably 4 cm larger than and more preferably 10 cm larger than the narrowest crotch width.

In an alternative embodiment the distance in transverse direction between the laterally outward sides of the leak barriers is equal to or smaller than narrowest crotch width.

According to one embodiment raised leak barriers are present in both the front and the back regions of the article.

According to one embodiment leak barriers are absent in the crotch region along a length (b) of at least 2 cm, preferably at least 5 cm and more preferably at least 10 cm, in longitudinal direction and that the leak barriers in the front and/or back regions have an end point in or adjacent the crotch region.

In a further embodiment the leak barriers extend along the crotch region but are deactivated in said region over a length (b) of at least at least 2 cm, preferably at least 5 cm and more preferably at least 10 cm, in longitudinal direction, by its laterally inward elasticized side being attached to the inner cover of the article, thus preventing it to raise.

By "deactivation" is meant that the leak barriers and the stretching in the leak barriers can remain but the leak barriers are laid flat in the deactivated region.

In a still further embodiment the leak barriers are at their respective end portions facing the transverse side edges and the crotch region respectively, laid flat and attached to the inner coversheet also at their laterally inward side, so that each leak barrier will form a pocket.

In one embodiment, the article is a pant type absorbent article such as a pant diaper, a sanitary pant or incontinence pant, said article having a core region comprising an absorbent core, and a chassis surrounding the core region, said chassis comprising front, back and waist regions, while the core region is located at least in the crotch region of the article, a liquid impermeable outer cover is arranged at least in the core region on the garment-facing side of the absorbent core and a liquid permeable inner cover is arranged at least in the core region on the wearer-facing side of the absorbent core,
said article in at least a part of the chassis region comprises an outer coversheet in the form of an elastic web material.

In a further aspect the leak barriers are arranged in the core region of the article. In a still further aspect the surface area of the absorbent core amounts to no more than 30%, preferably no more than 20%, of the total surface area of the article, as measured in a flat state of the article.

In a further embodiment, the above embodiments are applied to an absorbent article in the form of a diaper, a pant diaper or an incontinence garment.

DESCRIPTION OF DRAWINGS

The invention will in the following be closer described with reference to some embodiments, to which it is not limited, shown in the accompanying drawings.

DEFINITIONS

Absorbent Article

Figure 1:
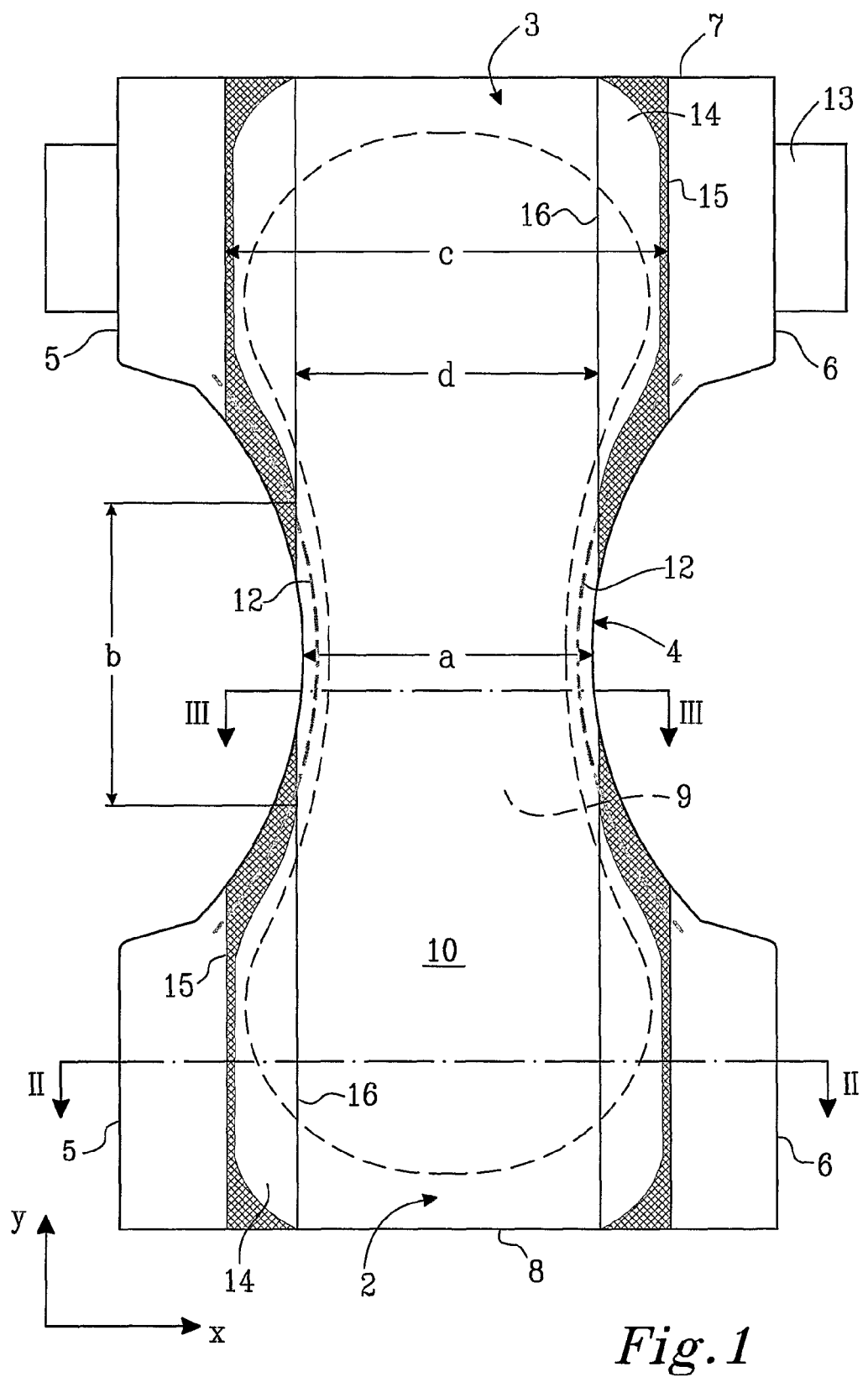
FIG. 1 shows a simplified plan view of an absorbent article in the form of a diaper in its flat, uncontracted state.

The term "absorbent article" refers to products that are placed against the skin of the wearer to absorb and contain body exudates, like urine, faeces and menstrual fluid. The disclosure mainly refers to disposable absorbent articles, which are articles that are not intended to be laundered or otherwise restored or reused as an absorbent article after use.

Inner Liquid Permeable Cover

The inner liquid permeable cover forms the inner cover of the absorbent article and in use is placed in direct contact with the skin of the wearer. The inner liquid permeable cover can comprise a nonwoven material, e.g. spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The inner liquid permeable cover material may further be composed of tow fibres, which may be bonded to each other in a bonding pattern, as e.g. disclosed in EP-A-1 035 818. Further examples of inner liquid permeable cover materials are porous foams, apertured plastic films etc. The materials suited as inner liquid permeable cover materials should be soft and non-irritating to the skin and be readily penetrated by body fluid, e.g. urine or menstrual fluid. The inner liquid permeable cover may further be different in different parts of the absorbent article.

Outer Liquid Impermeable Cover

The outer liquid impermeable cover forms the outer cover of the absorbent article at least on the core area thereof. The outer liquid impermeable cover can comprise a thin plastic film, e.g. a polyethylene or polypropylene film, a nonwoven material coated with a liquid impervious material, a hydrophobic nonwoven material, which resists liquid penetration, or a laminate, e.g. of a plastic film and a nonwoven material. The outer liquid impermeable cover material may be breathable so as to allow vapour to escape from the absorbent core, while still preventing liquids from passing through. Examples of breathable outer liquid impermeable cover materials are porous polymeric films, nonwoven laminates from spunbond and meltblown layers, laminates from porous polymeric films and nonwoven materials.

Absorbent Core

The absorbent core can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times its weight of an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Preferred superabsorbent materials are further surface crosslinked so that the outer surface or shell of the superabsorbent particle, fiber, flake, sphere, etc. possesses a higher crosslink density than the inner portion of the superabsorbent. The superabsorbent materials may be in any form suitable for use in absorbent composites including particles, fibers, flakes, spheres, and the like.

A high absorption capacity is provided by the use of high amounts of superabsorbent material. For an absorbent core comprising a matrix of hydrophilic fibers, such as cellulosic fibers, and superabsorbent material, the proportion of superabsorbent material is preferably between 10 and 90% by weight, more preferably between 30 and 70% by weight.

It is conventional in absorbent articles to have absorbent cores comprising layers of different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent polymers. The size and absorbent capacity of the absorbent core may be varied to be suited for different uses such as for infants or for adult incontinent persons.

The absorbent core may further include an acquisition distribution layer placed on top of the primary absorbent body and which is adapted to quickly receive and temporarily store discharged liquid before it is absorbed by the primary absorbent core. Such acquisition distribution layers are well known in the art and may be composed of porous fibrous waddings or foam materials.

Leak Barriers

Leak barriers, or as they also are called containment or barrier flaps, extend substantially longitudinally alongside the absorbent structure. These leak barriers have a free laterally inward elasticized side (distal side) and a laterally outward side (proximal side) attached to the inner cover of the article, wherein the elasticized distal side of the leak barrier is raised from the inner cover of the absorbent article. Such raised leak barriers help to reduce the occurrence of leakage of body exudates from the absorbent articles.

DESCRIPTION OF PREFERRED EMBODIMENTS

FIG. 1 shows a simplified plan view of an absorbent article in a flat, uncontracted state. The absorbent article shown in FIG. 1 is in the form of a diaper 1 having a longitudinal, y, and a transverse direction, x, and comprises, as seen in its longitudinal direction, a front region 2, a back region 3 and a crotch region 4 there between. The article is defined by a pair of longitudinal side edges 5 and 6 and a pair of transverse side edges 7 and 8. The crotch region 4 is defined by an inwardly directed leg contour in each longitudinal side edge 5 and 6 of the article.

In its most common form the diaper comprises an absorbent core 9 and a cover enclosing the absorbent core. Said cover comprises an inner liquid pervious cover 10 on the wearer facing side of the absorbent core 9 and an outer liquid impervious cover 11 on the garment facing side of the absorbent core. The inner liquid pervious cover 10 is often referred to as topsheet, while the outer liquid impervious cover 11 is often referred to as backsheet.

The inner cover 10 and the outer cover 11 extend outward beyond the peripheral edges of the absorbent core 9 and have their inner surfaces bonded to each other, e g by gluing or welding by heat or ultrasonic. The inner and outer cover materials may further be bonded, e.g. by adhesive, to the absorbent core 9.

The areas of the article adjacent the leg openings are along the longitudinal side edges provided with elastic members 12, which are bonded between the inner cover 10 and the outer cover 11 material layers in a stretched condition so as to provide elasticized leg openings of the diaper. Corresponding elastic members (not shown) may be arranged to extend in the transverse, x, direction in the front 2 and back region 3 adjacent the transverse side edges forming the waist opening of the diaper.

The elastic members 12 may alternatively be of a material that is activatable by some means, for example by heat, to an elastified state, wherein they may be attached to the article in an unstretched inactivated state and are subsequently activated to a contracted elastic state.

The back region 3 is provided with fasteners 13 attached thereto. The fasteners are intended to be fastened to the front region of the article to form a pant-like shape. The fasteners 13 may be in the form of adhesive tapes or hook elements adapted to attach to a loop material, for example in the form of a nonwoven material forming the outer coversheet of the diaper.

Figure 2:
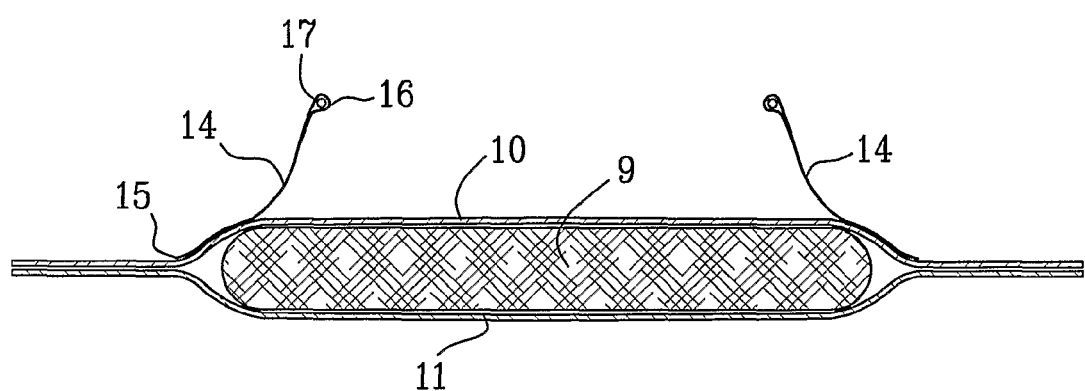
FIG. 2 is a section according to the line II-II in FIG. 1.
Figure 3:
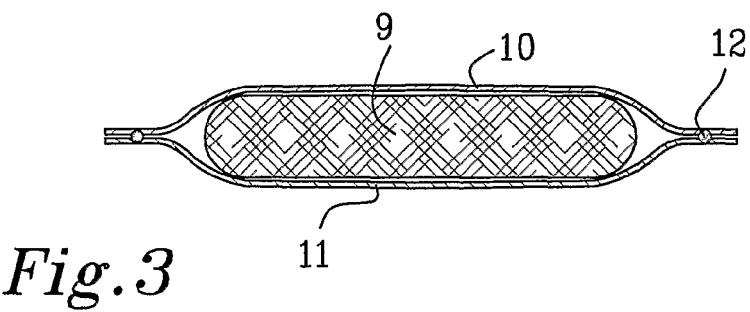
FIG. 3 is a section according to the line III-III in FIG. 1.

The diaper further comprises longitudinally extending elastic leak barriers 14 having a laterally outward proximal edge 15, a laterally inward distal edge 16 and elastic member 17 spacing the distal edge 16 away from the inner coversheet 10. These leak barriers 14 are at their proximal edges 15 attached to the inner coversheet 10 close to the lateral edges of the absorbent core 9 either laterally outside the absorbent core 9 or above the absorbent core 9. The attachment is made by for example adhesive, ultrasonic welding or heat bonding. In FIG. 1 the distal edges 16 of the leak barriers 14 are shown in an uncontracted state, in which they are not raised from the inner coversheet 10. In FIG. 2 however the leak barriers 14 are shown in their raised condition, in which their distal edges 16 are lifted from the inner coversheet 10.

According to the embodiment shown in FIG. 1 elastic leak barriers 14 are present in the front 2 and back regions 3 of the diaper while a substantial part of the crotch region 4 is free from elastic leak barriers 14. According to the disclosure the crotch region 4 is free from raised leak barriers along a length (b) of at least at least 2 cm, preferably at least 5 cm and more preferably at least 10 cm, in longitudinal direction.

The leak barriers 14 are at their respective end portions facing the transverse side edges 7 and 8 respectively, and the crotch region 4, laid flat and attached to the inner coversheet also at their distal edges for example by adhesive, ultrasonic welding, heat bonding or the like. The leak barriers 14 will herewith form pockets. In FIG. 1 the attached portions of the leak barriers 14 are shadowed.

In FIG. 1 the distance (c) between the proximal edges 15 of the two leak barriers 14 as well as the distance (d) between the distal edges 16, when in their uncontracted state lying flat against the inner coversheet 10, are equal to or larger than the minimum crotch width (a) of the diaper. The crotch width is also being measured with the diaper in an uncontracted state as shown in FIG. 1.

When manufacturing the diaper shown in FIG. 1 there are a couple of options available. A first alternative is to attach a continuous length of leak barriers 14 to the diaper before making cuts for the leg contours. When cuts are made for the leg contours the leak barriers are at the same time cut away at least in that portion of the crotch region 4 having the smallest crotch width. The distal edge 16 with the elastic member 17 is before the cut is made attached to the inner coversheet at the end facing the crotch region 4. The distal edge 16 is also attached to the inner coversheet at the end facing the respective transverse edge 7 and 8 of the diaper. The attachment of the distal end 16 with the elastic member 17 is made by adhesive, ultrasonic welding or heat bonding.

Another alternative is to intermittently attach discontinuous lengths of leak barriers 14 in the front and/or back regions 2 and 3, while leaving at least a part of the crotch region 4 free from leak barriers 4. The leak barriers 14 may be present in both the front and back regions 2 and 3 of the diaper, as shown in the drawings, or they may be present in only the front region 2 or only in the back region 3.

In an alternative embodiment the distance (c) between the proximal edges 15 of the two leak barriers 14 is equal to or smaller than the minimum crotch width (a) of the diaper and the distance (d) between the distal edges 16 of the leak barriers 14, when in their uncontracted state lying flat against the inner coversheet 6, is smaller than the minimum crotch width (a). In this case discontinuous lengths of leak barriers 14 are intermittently attached in the front and/or back regions 2 and 3, while leaving at least a part of the crotch region 4 free from leak barriers 4. An alternative option is to attach a continuous length of leak barriers 14 to the diaper extending over the crotch region 4 and to attach the distal edge 16 of the leak barrier 14 to the inner coversheet along at least a part of the crotch region 4, so that the leak barrier 14 will not form a raised leak barrier in said portion. The attached (inactivated) length of the distal edge 16 of the leak barrier 14 should be at least at least 2 cm, preferably at least 5 cm and more preferably at least 10 cm.

Figure 4:
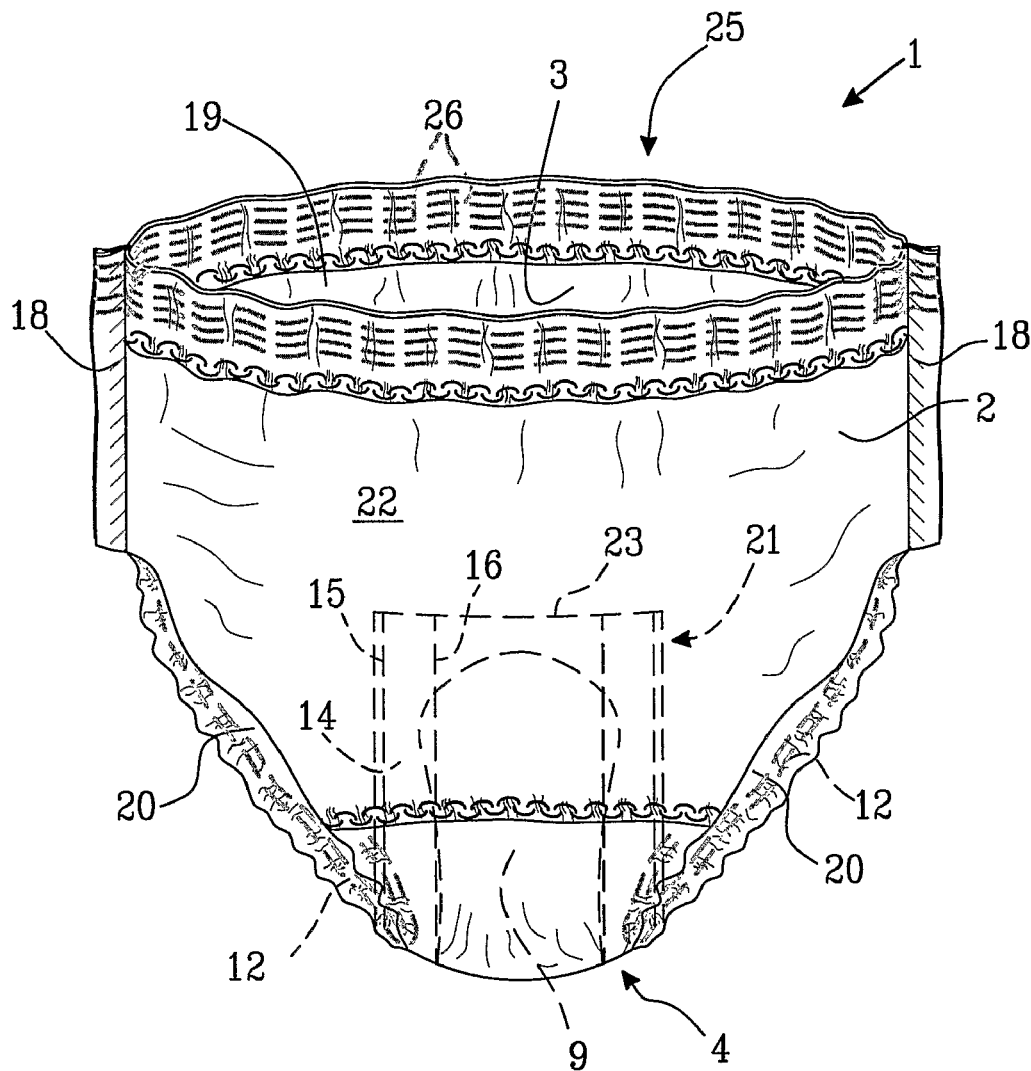
FIG. 4 shows a perspective view of a pant diaper.
Figure 5:
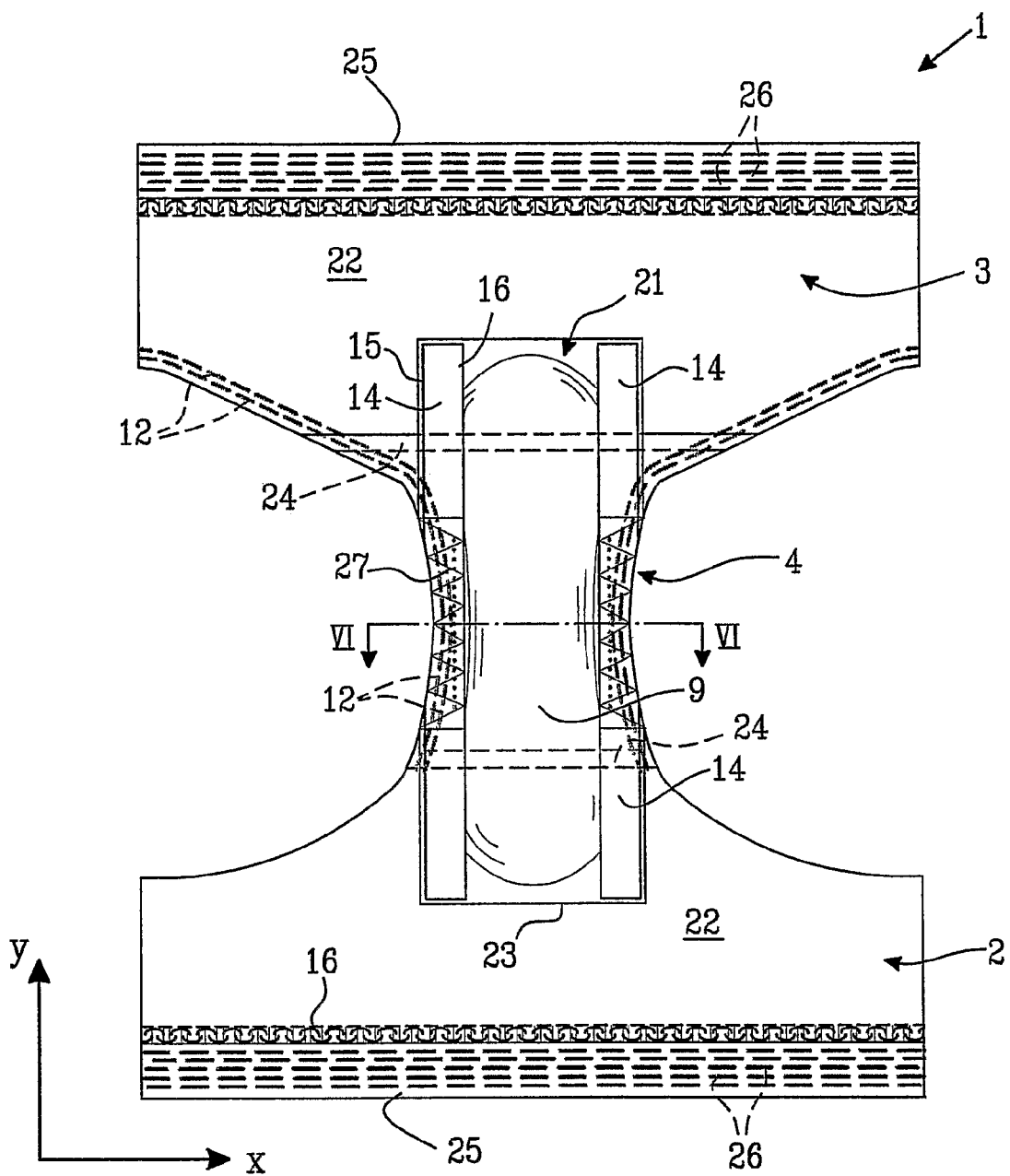
FIG. 5 shows is a plan view of the pant diaper in its flat, uncontracted state prior to formation as seen from the body facing side.
Figure 6:
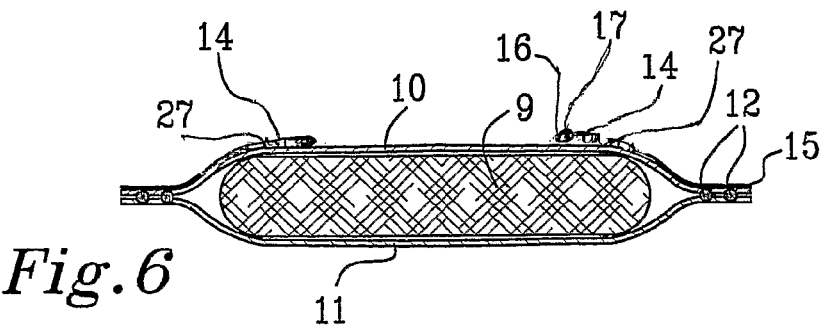
FIG. 6 is a section according to the line VI-VI in FIG. 5.

FIG. 4-6 show a further example of an absorbent article 1 in the form of a pant-type absorbent article, which may be a pant diaper, a sanitary pant or an incontinence pant. The front and back panels 2 and 3 of the pant article are joined to each other along their longitudinal side edges thereof forming side seams 18 to define a waist-opening 19 and a pair of leg-openings 20.

The pant article shown in FIG. 4-6 comprises a core region 21 comprising the absorbent core 9, a liquid pervious inner cover 10 and a liquid impervious outer cover 11 as disclosed above, and a chassis region outside the core region 21. The chassis comprises a front region 2, a back region 3 and a waist region comprising an elastic waistband 25. At least a part of the chassis region comprises a coversheet 22 of a soft and comfortable material in the form of an elastic web material, for example an elastic laminate. An example of such a pant article is disclosed in PCT/SE2004/1005 and PCT/SE2005/000307. Further details about the elastic laminate used as coversheet 22 may be found in any of these documents.

The elastic laminate 22 may cover the entire article, including the core region 21 and the entire front and back panels 2 and 3. However according to a preferred embodiment a substantial part of the crotch region 4 of the article is free from the elastic web material 22. A "substantial part" used herein refers to at least 50%, preferably at least 75%.

A crotch region web material 23, which preferably is a non-elastic nonwoven material, is arranged in the crotch region 4 of the article and overlaps with the elastic front and back panels 2 and 3. The crotch region web material 23 is joined in an overlapping manner to the front and back panels 2 and 3, respectively, by means of ultrasonic welds 24, heat bonding, cold bonding, glue strings or the like.

An elastic waist band 25 is further provided which comprises a substantially non-elastic nonwoven material that is elasticized by elongate elastic members 26 such as elastic threads, contractably affixed between material layers, such as nonwoven materials. Elastic threads 12 may also be arranged around the leg openings 5 and 6 of the article.

The liquid-impervious backsheet material 11 underlies the absorbent core 9 and adjacent areas immediately outside the absorbent core 9. The area covered by the liquid-impervious backsheet 11 is defined as the core region 21. The crotch nonwoven material 23 is arranged on the garment-facing side of the liquid-impervious backsheet 11 in the crotch region 4 of the article. The core region 21 extends into the front and back panels 2 and 3 so that the elastic web material 22 and the liquid impervious backsheet 11 overlap in the outer parts of the core region 21, wherein the elastic web material 22 is arranged on the garment facing side of the liquid impervious backsheet 11.

The surface area of the absorbent core 9 amounts to no more than 30%, preferably no more than 20%, of the total surface area of the article, as measured in a flat state of the article.

The elastic laminate 22 constitutes the sole component of at least parts of the front and back panels 2 and 3. In at least 20%, preferably at least 25%, more preferably at least 30% and most preferably at least 40% of the total surface area of the article, as seen in a flat state according to FIG. 5, the elastic laminate 22 constitutes the sole component of the front and back panels.

No additional elasticized side panels joining the front and back panels 2 and 3 are needed when using the elastic laminate 22.

Leak barriers 14 are arranged in the core region 21 of the pant article and extend alongside the absorbent core 9. In the embodiment shown in FIGS. 4-6 the crotch width (a) of the article is larger than the distance (d) between the distal edges of the leak barriers and approximately equal to the distance (c) between the proximal edges 15 of the leak barriers 14. The leak barriers 14 have been deactivated along a certain length thereof in the crotch region, by attaching the distal edge 16 of the leak barriers 14 to the inner coversheet 10. This is best illustrated in FIG. 6. This attachment 27 is made by adhesive, ultrasonic welding or heat bonding.

In an alternative embodiment leak barriers 14 are intermittently attached to the front and/or back region 2, 3 as described above. In a still further embodiment the distances between the proximal edges 15 as well as the distal edges 16 of the leak barriers are larger than or equal to the crotch width of the pant article, wherein a continuous length of leak barriers may be attached alongside the core region 21 and then cut away when cutting the leg opening contours, in a manner described above with reference to FIG. 1.

Embodiments of the invention may be applied to any type of absorbent article having raised leakage barriers. It is especially useful in articles having a narrow crotch width of no more than 20 cm, preferably no more than 15 cm as the smallest crotch width (a). Having raised leak barriers in the crotch region of absorbent articles with a narrow crotch width, may cause a leakage problem, especially when the leakage barriers do not completely raise from the inner coversheet of the article. The leakage barrier may then partly block the entry of body fluid into the crotch area of the article. This problem is solved by embodiments of the invention, while the front and/or back region of the article still benefit from the leakage barriers. In the crotch region a tight fit around the leg opening is often provided by the leg elastics, which will prevent leakage in this area. An improved comfort and fit in the crotch region is further accomplished by embodiments of the present invention.

Although the present disclosure has been described with reference to certain preferred embodiments, it is apparent that modifications and variations thereof may be made by those skilled in the art without departing from the scope of the disclosure as defined by the following claims.

The invention claimed is:

1. An absorbent article comprising an absorbent core and a cover enclosing the absorbent core, said cover comprising a liquid pervious inner cover on a wearer facing side of the absorbent core and a liquid impervious outer cover on a garment facing side of the absorbent core, said article having a longitudinal and a transverse direction and being defined by a pair of longitudinal side edges and a pair of first transverse side edges, said article comprises, as seen in the longitudinal direction of the article, a front region, a back region and a crotch region there between, said crotch region being defined by an inwardly directed leg contour in each longitudinal side edge of the article, wherein at least part of the crotch region has a width in the transverse direction of no more than 20 cm,
said article further comprises substantially longitudinally extending leak barriers, each of said leak barriers having a free laterally inward elasticized side, a laterally outward side and a plurality of second transverse side edges, portions of the elasticized side of the leak barrier between the second transverse side edges being raised from the inner cover of the absorbent article,
a majority of an inward side of at least one second transverse side edge of the leak barrier extending between the free laterally inward elasticized side and the laterally outward side being adjoined to the inner cover,
wherein the crotch region along a length of at least 2 cm, in the longitudinal direction is free from raised leak barriers, while raised leak barriers are present in the front or back regions of the article.

2. An absorbent article as claimed in claim 1,
wherein the distance in transverse direction between the laterally outward sides of the leak barriers is at least at least 3 cm.

3. An absorbent article as claimed in claim 2,
wherein the distance in transverse direction between the laterally outward sides of the leak barriers is at least equal to or larger than the narrowest width in transverse direction in the crotch region.

4. An absorbent article as claimed in claim 3,
wherein the distance in transverse direction between the laterally outward sides of the leak barriers is at least 4 cm larger than the narrowest width in transverse direction in the crotch region.

5. An absorbent article as claimed in claim 1,
wherein the distance in transverse direction between the laterally outward sides of the leak barriers is equal to or smaller than the width of the crotch region in the narrowest portion thereof.

6. An absorbent article as claimed in claim 1,
wherein raised leak barriers are present in both the front and the back regions of the article.

7. An absorbent article as claimed in claim 1,
wherein leak barriers are absent the crotch region along a length of at least 2 cm in longitudinal direction and that the leak barriers in the front and/or back regions have an end point in or adjacent the crotch region.

8. An absorbent article as claimed in claim 1,
wherein the leak barriers extend along the crotch region, but are deactivated in said region over a length of at least 2 cm in longitudinal direction, each leak barrier being attached to the inner cover of the article at the inward side between the free laterally inward elasticized side and the laterally outward side at the second transverse side edges, thus preventing each leak barrier to raise.

9. An absorbent article as claimed in claim 1,
wherein respective second transverse side edges of the leak barriers adjoining the first transverse side edges, and the crotch region respectively, lie flat and are attached to the inner coversheet at their inward side, so that each leak barrier will form a pocket.

10. An absorbent article as claimed in claim 1,
wherein said article is a pant type absorbent article, said article having a core region comprising an absorbent core, and a chassis surrounding the core region, said chassis comprising front, back and waist regions, while the core region is located at least in the crotch region of the article, a liquid impermeable outer cover is arranged at least in the core region on the garment-facing side of the absorbent core and a liquid permeable inner cover is arranged at least in the core region on the wearer-facing side of the absorbent core, said article in at least a part of the chassis region comprises an outer coversheet in the form of an elastic web material.

11. An absorbent article as claimed in claim 10,
wherein leak barriers are arranged in the core region of the article.

12. An absorbent article as claimed in claim 10,
wherein the surface area of the absorbent core amounts to no more than 30% of the total surface area of the article, as measured in a flat state of the article.

* * * * *